United States Patent
Iwama

(10) Patent No.: US 12,306,426 B2
(45) Date of Patent: May 20, 2025

(54) RADIATION PROBE WITH RADIAL SCATTER REGIONS WITH VARIOUS INTENSITIES

(71) Applicant: FURUKAWA ELECTRIC CO., LTD., Tokyo (JP)

(72) Inventor: Masaki Iwama, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 18/587,093

(22) Filed: Feb. 26, 2024

(65) Prior Publication Data

US 2024/0192421 A1 Jun. 13, 2024

Related U.S. Application Data

(63) Continuation of application No. PCT/JP2022/031109, filed on Aug. 17, 2022.

(30) Foreign Application Priority Data

Aug. 27, 2021 (JP) .................................. 2021-139394

(51) Int. Cl.
  *G02B 6/00* (2006.01)
  *F21V 8/00* (2006.01)
  *A61N 5/06* (2006.01)

(52) U.S. Cl.
  CPC .............. *G02B 6/001* (2013.01); *A61N 5/062* (2013.01); *A61N 2005/063* (2013.01)

(58) Field of Classification Search
  CPC .............. A61N 2005/063; G02B 6/001; G02B 6/0008; G02B 6/0035
  See application file for complete search history.

(56) References Cited

U.S. PATENT DOCUMENTS

| 5,632,767 A | 5/1997 | Sinofsky |
| 5,637,877 A | 6/1997 | Sinofsky |

(Continued)

FOREIGN PATENT DOCUMENTS

| JP | 56-242 Y2 | 1/1981 |
| JP | 2005-143576 A | 6/2005 |

(Continued)

OTHER PUBLICATIONS

Mch Translation of Weisberg Ref JP2015510142 (Year: 2015).*
International Search Report issued Oct. 25, 2022 in PCT/JP2022/031109 filed on Aug. 17, 2022, 4 pages.

*Primary Examiner* — Robert J May
(74) *Attorney, Agent, or Firm* — Oblon, McClelland, Maier & Neustadt, L.L.P.

(57) ABSTRACT

A radiation probe includes: an optical fiber including a leak section configured to output leaking light to an outer side in a radial direction as at least a part of a section in a longitudinal direction. The optical fiber includes a scattering area configured to generate the leaking light by scattering light in a predetermined area in a circumferential direction of the optical fiber in the leak section, and the optical fiber has directionality by which an intensity of the leaking light in two radial directions that are approximately parallel to each other is higher than an intensity of the leaking light in another radial direction in an intensity distribution of the leaking light in the circumferential direction in a cross-section intersecting an axial direction of the leak section.

17 Claims, 9 Drawing Sheets

(56) References Cited

U.S. PATENT DOCUMENTS

| | | |
|---|---|---|
| 5,643,253 A | 7/1997 | Baxter et al. |
| 5,908,415 A | 6/1999 | Sinofsky |
| 5,947,959 A | 9/1999 | Sinofsky |
| 6,102,905 A | 8/2000 | Baxter et al. |
| 6,168,591 B1 | 1/2001 | Sinofsky |
| 6,270,492 B1 | 8/2001 | Sinofsky |
| 6,423,055 B1 | 7/2002 | Farr et al. |
| 6,558,375 B1 | 5/2003 | Sinofsky et al. |
| 6,572,609 B1 | 6/2003 | Farr et al. |
| 6,579,285 B2 | 6/2003 | Sinofsky |
| 6,626,900 B1 | 9/2003 | Sinofsky et al. |
| 6,676,656 B2 | 1/2004 | Sinofsky |
| 6,942,657 B2 | 9/2005 | Sinofsky et al. |
| 6,953,457 B2 | 10/2005 | Farr et al. |
| 7,207,984 B2 | 4/2007 | Farr et al. |
| 7,357,796 B2 | 4/2008 | Farr et al. |
| 7,935,108 B2 | 5/2011 | Baxter et al. |
| 8,025,661 B2 | 9/2011 | Arnold et al. |
| 8,152,795 B2 | 4/2012 | Farr et al. |
| 8,231,613 B2 | 7/2012 | Baxter et al. |
| 8,241,272 B2 | 8/2012 | Arnold et al. |
| 8,267,932 B2 | 9/2012 | Baxter et al. |
| 8,277,444 B2 | 10/2012 | Arnold et al. |
| 8,366,705 B2 | 2/2013 | Arnold et al. |
| 8,444,639 B2 | 5/2013 | Arnold et al. |
| 8,540,704 B2 | 9/2013 | Melsky et al. |
| 8,900,219 B2 | 12/2014 | Sinofsky et al. |
| 9,033,961 B2 | 5/2015 | Melsky et al. |
| 9,421,066 B2 | 8/2016 | Melsky et al. |
| 9,861,437 B2 | 1/2018 | Melsky et al. |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0167503 A1 | 8/2004 | Sinofsky |
| 2005/0222558 A1 | 10/2005 | Baxter et al. |
| 2005/0234436 A1 | 10/2005 | Baxter et al. |
| 2005/0234437 A1 | 10/2005 | Baxter et al. |
| 2009/0275934 A1 | 11/2009 | Baxter et al. |
| 2010/0152721 A1 | 6/2010 | Tsumanuma et al. |
| 2012/0330293 A1 | 12/2012 | Arai et al. |
| 2013/0012923 A1 | 1/2013 | Baxter et al. |
| 2014/0031802 A1 | 1/2014 | Melsky et al. |
| 2014/0288541 A1 | 9/2014 | Eshkol et al. |
| 2014/0330261 A1 | 11/2014 | Arai et al. |
| 2016/0157928 A1 | 6/2016 | Eshkol et al. |
| 2018/0235700 A1 | 8/2018 | Eshkol et al. |
| 2022/0397262 A1* | 12/2022 | Schultheis ............ G02B 6/241 |

FOREIGN PATENT DOCUMENTS

| | | |
|---|---|---|
| JP | 3675482 B2 | 7/2005 |
| JP | 2011-145520 A | 7/2011 |
| JP | 5113400 B2 | 1/2013 |
| JP | 2015-510142 A | 4/2015 |
| WO | WO 2011/105631 A1 | 9/2011 |

* cited by examiner

X

RADIATION PROBE WITH RADIAL SCATTER REGIONS WITH VARIOUS INTENSITIES

This application is a continuation of International Application No. PCT/JP2022/031109, filed on Aug. 17, 2022 which claims the benefit of priority of the prior Japanese Patent Application No. 2021-139394, filed on Aug. 27, 2021, the entire contents of which are incorporated herein by reference.

BACKGROUND

The present invention relates to a radiation probe.

Medical probes usable in photodynamic therapy (PDT) and photoimmunotheray (PIT), photodynamic diagnosis (PDD), etc., have been known (for example, Japanese Patent No. 5113400).

As for probes of this type, a radiation probe whose circumference is partially shielded by a reflective element in order to provide directionality to radiation light is known (for example, Japanese Patent No. 3675482).

SUMMARY

The configuration according to Japanese Patent No. 3675482 has a problem in that, because it is necessary to cover all the area excluding an area to which light is to be radiated, the radiation probe is thick.

In general, an optical radiation probe that is used for PDT and PIT has a structure in which a scattering surface extending in a longitudinal direction along the entire circumference is formed on a flexible plastic fiber and light is scattered from the scattering surface. This case however has a problem of a risk that that the scattering surface generates heat when light is radiated and the limit of resistance to heat of the fiber is exceeded particularly when light of a high output is radiated.

There is a need for a radiation probe with an improved and novel configuration that has a small diameter and that makes it possible to obtain higher directionality and further reduce heat generation.

According to one aspect of the present disclosure, there is provided a radiation probe including: an optical fiber including a leak section configured to output leaking light to an outer side in a radial direction as at least a part of a section in a longitudinal direction, wherein the optical fiber includes a scattering area configured to generate the leaking light by scattering light in a predetermined area in a circumferential direction of the optical fiber in the leak section, and the optical fiber has directionality by which an intensity of the leaking light in two radial directions that are approximately parallel to each other is higher than an intensity of the leaking light in another radial direction in an intensity distribution of the leaking light in the circumferential direction in a cross-section intersecting an axial direction of the leak section.

According to another aspect of the present disclosure, there is provided a radiation probe including: an optical fiber including a leak section configured to output leaking light to an outer side in a radial direction as at least part of a section in a longitudinal direction, wherein the optical fiber has directionality by which an intensity of the leaking light in a specific radial direction is higher than an intensity of the leaking light in another radial direction in an intensity distribution of the leaking light in a circumferential direction in a cross-section intersecting an axial direction of the leak section; and a reflective member positioned differently in a specific radial direction with respect to the optical fiber and configured to reflect the leaking light.

According to still another aspect of the present disclosure, there is provided a radiation probe including: an optical fiber including a leak section that outputs leaking light to an outer side in a radial direction as at least part of a section in a longitudinal direction, wherein the optical fiber has directionality by which an intensity of the leaking light in a specific radial direction is higher than an intensity of the leaking light in two radial directions that are approximately parallel is higher than an intensity of the leaking light in another radial direction in an intensity distribution of the leaking light in a circumferential direction in a cross-section intersecting an axial direction of the leak section; and a reflective member positioned differently in one of two radial directions that are approximately parallel to each other with respect to the optical fiber and configured to reflect the leaking light.

DETAILED DESCRIPTION

Figure 1:
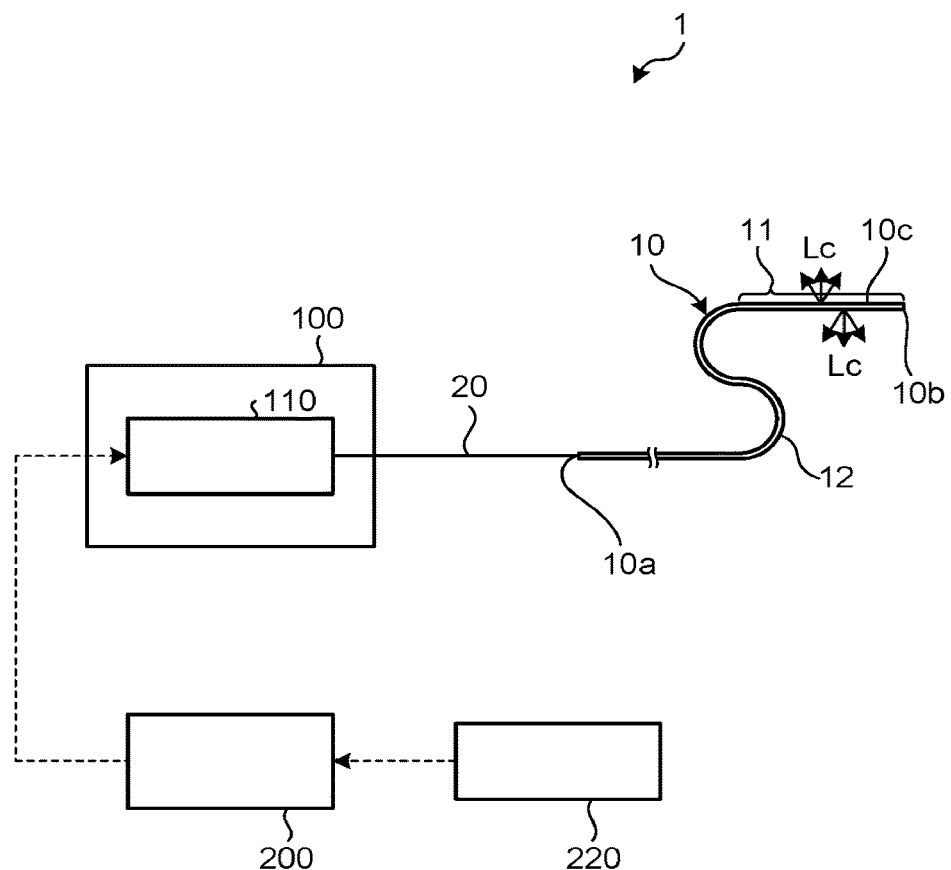
FIG. 1 is an exemplary schematic configuration diagram of a radiation probe system of an embodiment.

An exemplary embodiment and a modification will be described below. Configurations of the embodiment and the modification presented below and the functions and results (effects) caused by the configurations are an example. The present invention can be realized also by configurations other than those disclosed in the following embodiments and modifications. According to the present invention, it is possible to obtain at least one of various effects (including derivative effects) that are obtained because of the configurations.

The embodiments and modifications presented below have similar configurations. Thus, according to each of the embodiments and the modifications, similar functions and effects based on the similar configurations are obtained. Similar reference numerals are assigned to the similar configurations and redundant description is sometimes omitted below.

In the specification, ordinal numbers are assigned for convenience in order to distinguish parts, portions, etc., and do not represent priorities and an order.

In each of the drawings, an X-direction is an axial direction (longitudinal direction) of a radiation probe 10 and an optical fiber 30.

FIG. 1 is a schematic diagram of a radiation probe system 1 of the embodiment. As illustrated in FIG. 1, the radiation probe system 1 includes a light output device 100, a radiation probe 10, a control device 200, a delivery optical fiber 20, and an input unit 220.

The light output device 100 includes a light source unit 110. The light source unit 110 includes a light source that outputs laser light, an optical system that guides the light from the light source to the delivery optical fiber 20 (neither of them is illustrated). The light source includes, for example, a laser element that outputs laser light.

The light source unit 110 and the radiation probe 10 are optically connected via the delivery optical fiber 20.

The radiation probe 10 includes an optical fiber, has an elongated approximately cylindrical and liner shape, and has flexibility. The radiation probe 10 has an end 10a that is an end in an axial direction and an end 10b that is the other end in the axial direction. The end 10a is an input end to which the light from the light source unit 110 is input and the end 10a cab be also referred to a base end. The end 10b is positioned on a side opposite to the end 10a in the axial direction and the end 10b can be also referred to a distal end.

The radiation probe 10 includes a leak portion 11 and a transmission portion 12. The leak portion 11 is a section that is provided along a predetermined length in the axial direction in a position distant from the end 10a and that leaks light from an outer circumferential surface 10c of the radiation probe 10 to an outer side in a radial direction. The leaking light from the outer circumferential surface 10c is radiation light from the radiation probe 10. The transmission portion 12 is a section that transmits light between the end 10a and the leak portion 11, between the leak portion 11 and the end 10b, or, in the case where a plurality of the leak portions 11 are provided at intervals in the axial direction, between two leak portions 11 with the interval in between. In the embodiment, the leak portion 11 is provided only in the section adjacent to the end 10b as an example; however, the leak portion 11 is not limited thereto and the leak portion 11 may be provided apart from the end 10b.

The control device 200 is capable of controlling the light source unit 110 such that light source unit 110 outputs light or stops the output. The control device 200 is also able to control operations of a device or a part other than the light source unit 110 in the radiation probe system 1. The input unit 220 configures a user interface that is operated by an operator (user) and inputs an instruction signal corresponding to an operation input made by the operator to the control device 200. The control device 200 is an example of a control system and the input unit 220 is an example of the operation input unit.

Figure 2:
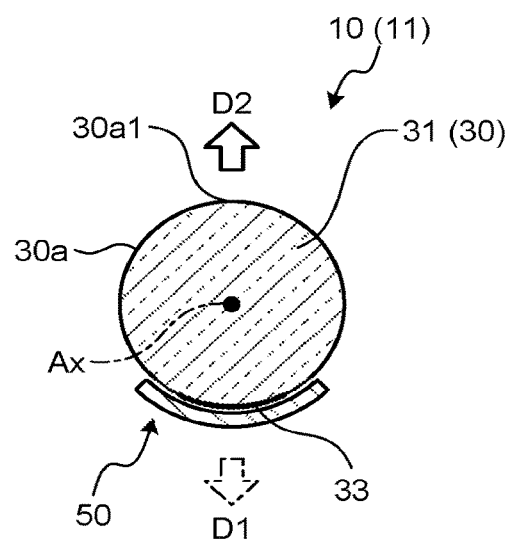
FIG. 2 is an exemplary and schematic cross-sectional view of the radiation probe of the embodiment.

FIG. 2 is a cross-sectional view of the leak portion 11 of the radiation probe 10. The radiation probe 10 includes the optical fiber 30 and a reflective member 50 that are illustrated in FIG. 2 and a coating (not illustrated in the drawing) that surrounds the optical fiber 30 and the reflective member 50. The coating has transmittance to light that is transmitted via the optical fiber 30.

The optical fiber 30 is optically connected to the delivery optical fiber 20. The optical fiber 30 and the delivery optical fiber 20 may be connected directly by fusion or indirectly via a joint, or the like, or the optical fiber 30 and the delivery optical fiber 20 may be made of a single optical fiber.

The optical fiber 30 includes a core 31 and a cladding (not illustrated in the drawing) that surrounds the core 31. In the transmission portion 12, the optical fiber 30 includes the core 31 and the cladding. On the other hand, in the leak portion 11, for example, as illustrated in FIG. 2, the cladding is almost removed from each optical fiber 30 and only the core 31 is present. In other words, in the example in FIG. 2, an outer circumferential surface 30a of each optical fiber 30 is an outer circumferential surface of the core 31.

In the leak portion 11, at least one of the outer circumferential surface 30a and an area at a predetermined depth near the outer circumferential surface 30a is provided with a scattering area 33 that scatters light. The scattering area 33 extends in a circumferential direction. Specifically, the scattering area 33 is provided in a section in the circumferential direction in a cross-section of the optical fiber 30 orthogonal to a center axis Ax, specifically, in a fan-shaped arc having a predetermined center angle (for example, 60 deg as an example in FIG. 2) or an area near the arc.

Although not illustrated in the drawings, the scattering area 33 extends also in the axial direction (longitudinal direction). In other words, the scattering area 33 is provided over a predetermined section in the longitudinal direction in the leak portion 11. The scattering area 33 may be provided over the entire area of the leak portion 11, may be provided partly, or may be provided intermittently in a plurality of spots in the leak portion 11. When a plurality of the scattering areas 33 are provided in the leak portion 11, the scattering areas 33 are provided in an aligned manner in the longitudinal direction. In the optical fiber 30, the section in which the scattering area 33 is provided is an example of a leak section. The leak section is contained in the leak portion. In other words, the leak section in which the scattering area 33 is provided in the optical fiber 30 is part of components of the leak portion 11 of the radiation probe 10.

Figure 3:
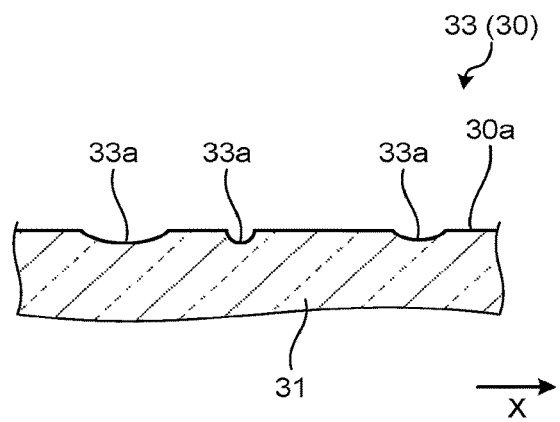
FIG. 3 is an exemplary and schematic cross-sectional view of part of an optical fiber of the radiation probe of the embodiment.

FIG. 3 is a cross-sectional view of the optical fiber 30 in a portion in which the scattering area 33 is provided. As illustrated in FIG. 3, in the scattering area 33, the outer circumferential surface 30a is provided with a plurality of concave portions 33a. The light that is transmitted through the core 31 bents at the concave portions 33a and is scattered and leaks from the outer circumferential surface 30a to the outside of the core 31, that is, to the outside of the optical fiber 30.

In the example in FIG. 3, the concave portions 33a are provided dispersedly and the concave portions 33a are not constant in size and depth. This is however an example and the concave portions 33a may be arrayed regularly or the concave portions 33a may be approximately constant in specifications, such as the size, depth, and shape. In the scattering area 33, the outer circumferential surface 30a may be provided with convex portions instead of the concave portions 33a. The convex portions may be a portion between the concave portion 33a and the concave portion 33a. In the embodiment, the concave portions 33a and the convex portions promote the light to leak from the core 31 to the outer side in the radial direction. Appropriately adjusting the positions in which the concave portions 33a and the convex portions are set and the specification, such as the setting density, size, and depth, makes it possible to adjust the distribution of intensity of leak of light in the axial direction and the circumferential direction in the leak portion 11.

In the example in FIG. 2, an average curvature radius in the scattering area 33 is equal to a radius of a general area of the outer circumferential surface 30a of the optical fiber 30 where the scattering area 33 is not formed. In this case, the outer circumferential surface 30a is a convex curved surface in the scattering area 33.

Appropriately providing the scattering area 33 described above in the optical fiber 30 makes it possible to configure the optical fiber 30 as an optical fiber in which, in an intensity distribution of the leaking light in a circumferential direction on a cross-section intersecting the axial direction, the intensity of the leaking light in a specific radial direction (the outer side in the radial direction) from the center axis Ax of the optical fiber 30 is higher than the intensity of the leaking light in another radial direction, that is, as an optical fiber having directionality.

In the example in FIG. 2, in each optical fiber 30, the intensity of the leaking light in radial directions D1 and D2 is higher than those in other radial directions. The radial direction D1 and the radial direction D2 are radial directions different from each other and are directions that are approximately antiparallel to each other, that is, approximately opposite directions. By configuring the scattering area 33 appropriately, it is also possible to make the intensity of the leaking light in the radial direction D1 and the intensity of the leaking light in the radial direction D2 different from each other. The radial directions D1 and D2 are an example of the specific radial direction. Note that, in the specification, the specific radial direction is a radial direction in which the leaking light from the optical fiber 30 is at a peak in the intensity distribution in the circumferential direction of the optical fiber 30. When there are a plurality of radial directions (for example, two directions) enabling a peak, each of the directions is the specific radial direction.

Note that, the reflective member 50 is provided in the embodiment. As illustrated in FIG. 2, the reflective member 50 is positioned differently in the radial direction D1 from the optical fiber 30. In other words, in the embodiment, both the scattering area 33 and the reflective member 50 are positioned differently in the radial direction D1 from the center axis Ax, that is, in the same radial direction. The reflective member 50 reflects the scattering light that is incident on the reflective member 50. The leaking light, that is, the radiation light is not output from the radiation probe 10 in the radial direction D1. The radial direction D1 is an example of a first radial direction.

The reflective member 50, for example, contains a metal member and reflects the light leaking from the optical fiber 30. Note that the reflective member 50, for example, may include a body that is made of a material, such as a synthetic resin material, more flexible than a metal material and a reflective layer that covers the surface of the body on the side of the optical fiber 30 and that is made of a reflective material, such as a metal material.

In such a configuration, part of the light (scattering light) that is scattered in the scattering area 33 and that travels in the radial direction D2 of the optical fiber 30 undergoes total reflection on a surface of the optical fiber 30 on the side opposite to the scattering area 33 (referred to as an opposing surface 30a1 below) and remains in the optical fiber 30. Part of other light that is scattered in the scattering area 33 and that travels in the radial direction D2 of the optical fiber 30 does not meet a condition for total reflection on the opposing surface 30a1, leaks from the opposing surface 30a1 to the outside of the optical fiber 30, and travels in the radial direction D2 or a direction close to the radial direction D2.

On the other hand, most of the light that is scattered in the scattering area 33 and that travels in the radial direction D1 of the optical fiber 30 (scattering light) is reflected on the reflective member 50 and travels in the radial direction D2 or a direction close to the radial direction D2. Most of the light that is reflected on the reflective member 50 enters the optical fiber 30 again and travels toward the opposing surface 30a1. The opposing surface 30a1 divides the light remaining in the optical fiber 30 and the light that is output from the opposing surface 30a1 in the radial direction D2 or the direction close to the radial direction D2.

As described above, in the configuration of the embodiment, most of the scattering light in the scattering area 33 is emitted from the opposing surface 30a1 to the outside of the optical fiber 30 selectively, that is, leaks to the outside of the optical fiber 30.

Figure 18:
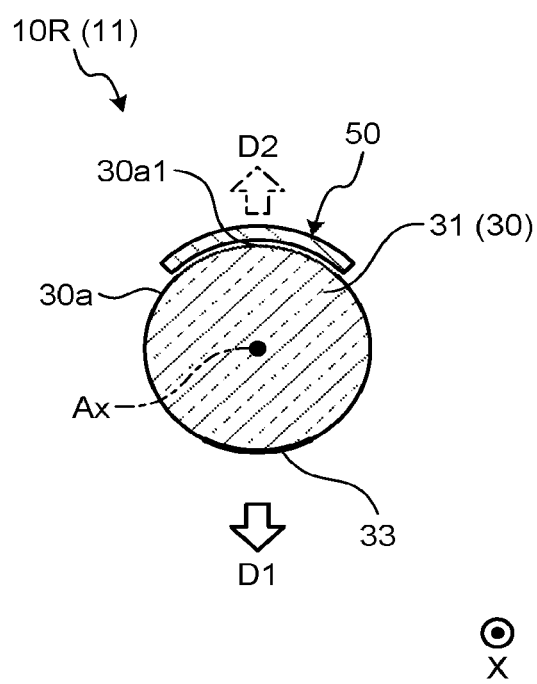
FIG. 18 is an exemplary and schematic cross-sectional view of a radiation probe of a reference example.

As illustrated in FIG. 18 that is a cross-sectional view of the leak portion 11 of a radiation probe 10R of a reference example, if the scattering area 33 and the reflective member 50 are positioned differently in radial directions approximately antiparallel to each other with respect to the center axis Ax, all the scattering light that is scattered from the scattering area 33 to the outside of the optical fiber 30 is output as leaking light and the directionality lowers. In this respect, according to the configuration in which the scattering area 33 and the reflective member 50 are positioned differently in the same radial direction with respect to the center axis Ax as in the layout of the above-described embodiment, most of the leaking light passes through the opposing surface 30a1. Thus, the leaking light is filtered on the opposing surface 30a1 and the directionality of the radiation probe 10 in the radial direction D2 increases correspondingly.

The reflective member 50 has a shape receding in the radial direction D1. The reflective member 50 thus functions as a concave mirror and the convergence of the reflected light in the radial direction D2 increases, which enables a further increase in directionality of the radiation probe 10 in the radial direction D2. The curvature radius of the reflective surface of the reflective member 50 may be equal to or different from the radius of the outer circumferential surface 30a.

The reflective member 50 extends to both sides in the circumferential direction with respect to the scattering area 33. Furthermore, the reflective member 50 makes contact with the scattering area 33 or faces the scattering area 33 with a minute gap in between. This lowers the ratio of direct leakage of the scattering light from the scattering area 33 to the outside of the optical fiber 30, in other words, further increases the ratio of leakage of the scattering light in the scattering area 33 to the outside of the optical fiber 30 via the opposing surface 30a1, which further easily increases directionality of the radiation probe 10 in the radial direction D2.

As for the configuration including the reflective member 50, it is preferable that the scattering area 33 be configured appropriately and thus the optical fiber 30 have directionality by which the intensity of the leaking light in the radial direction D2 is higher than the intensity of the leaking light in the radial direction D1. Accordingly, for example, an advantage that it is possible to inhibit heat generation in the reflective member 50 is obtained.

Furthermore, as illustrated in FIG. 2, because the reflective member 50 can be configured relatively narrower (smaller) along a relatively short area of the outer circumference of the optical fiber 30, an advantage that the radiation probe 10 can be configured thinner can be also obtained.

When the scattering area has a coarse surface, the scattering area generates heat when irradiated with light in some cases. In this respect, according to the configuration in FIG. 2, compared to the configuration in which the scattering area is formed over the entire circumference as conventional, it is possible to reduce the area of portion of heat generation per unit volume of the fiber and inhibit heat generation correspondingly.

Figure 4:
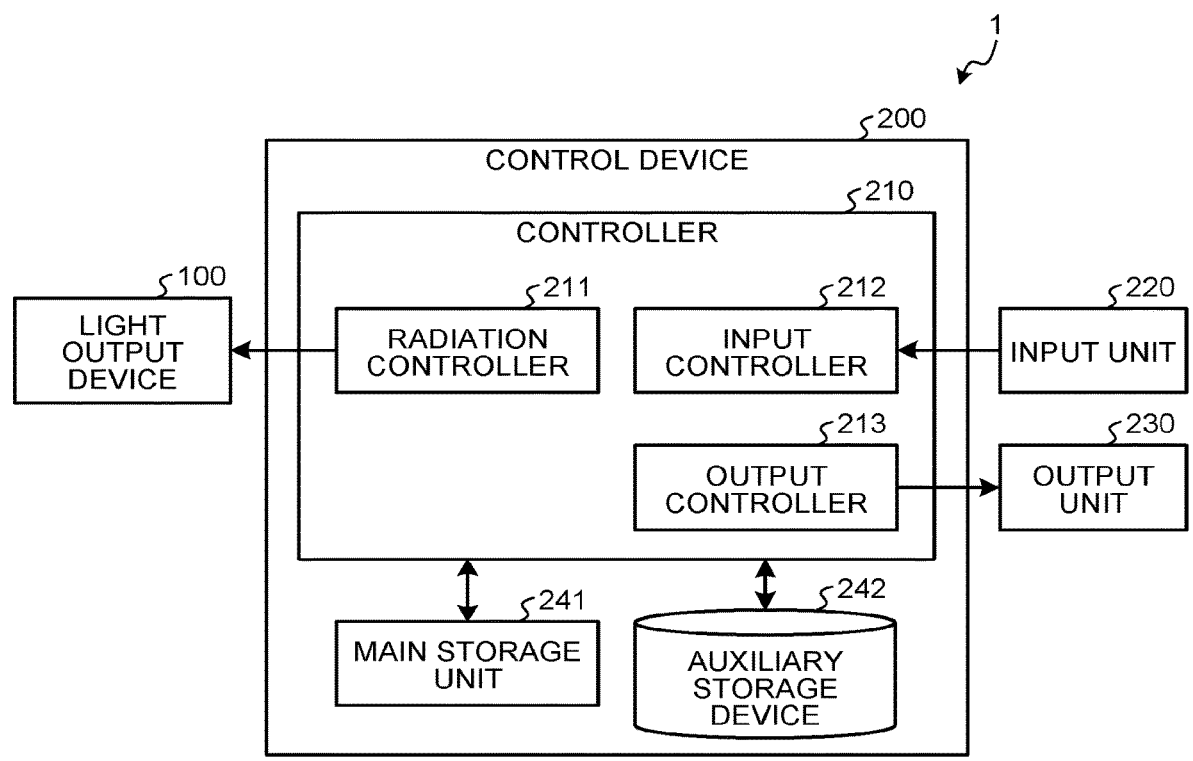
FIG. 4 is an exemplary block diagram of the radiation probe system of the embodiment.

FIG. 4 is a block diagram of the radiation probe system 1. As illustrated in FIG. 4, the radiation probe system 1 includes a control device 200, the input unit 220, and an output unit 230. The input unit 220 and the output unit 230 construct a user interface for a user or an operator. The input unit 220 is, for example, an operation unit, such as a remote controller, a switch box, or a joystick, or an input device, such as a keyboard, a touch panel, a mouse, a switch or an operation button. The output unit 230 is, for example, an output device, such as a display, a printer, a lamp, or a speaker, using images, printing, and sound.

The control device 200 includes a controller 210, a main storage unit 241, and an auxiliary storage device 242.

The controller 210 is, for example, a processor (circuitry), such as a CPU (central processing unit). The main storage unit 241 is, for example, a RAM (random access memory) or a ROM (read only memory). The auxiliary storage device 242 is, for example, a non-volatile rewritable storage device, such as a SSD (solid state drive) or a HDD (hard disk drive).

The controller 210 operates as a radiation controller 211, an input controller 212, and an output controller 213 by executing programs that are stored in the main storage unit 241 or the auxiliary storage device 242 and executing each of processes. Each of the programs can be recorded and provided in a computer-readable recording medium in a file in an installable form or an executable form. The recording medium can be also referred to as a program product. The programs and information, such as values, maps, and tables that are used in computation by a processor, may be stored previously in the main storage unit 241 or the auxiliary storage device 242 or may be stored in a storage unit of a computer that is connected to a communication network and may be downloaded via the communication network and accordingly may be stored in the auxiliary storage device 242. The auxiliary storage device 242 stores data that is written by the processor. The computation by the controller 210 may be executed at least partly by hardware. In this case, the controller 210 may contain a FPGA (field programmable gate array), an ASIC (application specific integrated circuit), or the like.

The radiation controller 211 is able to have control on the light source unit 110 contained in the light output device 100 in outputting light or stopping the output in response to an operation input of the operator to the input unit 220.

The input controller 212 receives an input signal from the input unit 220. The input controller 212 may control the input unit 220 such that a predetermined operation input is enabled.

The output controller 213 controls the output unit 230 such that the output unit 230 executes a predetermined output.

Figure 5:
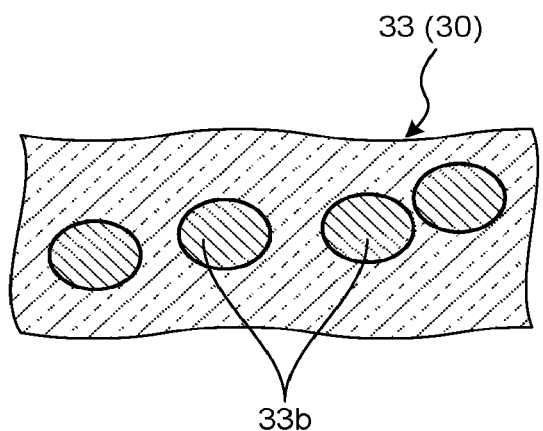
FIG. 5 is a schematic cross-sectional view of a modification of a scattering area of the radiation probe of the embodiment.
Figure 6:
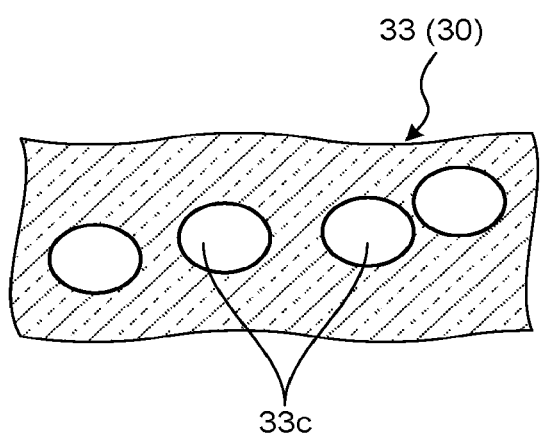
FIG. 6 is a schematic cross-sectional view of the modification of the scattering area of the radiation probe of the embodiment.

Each of FIG. 5 and FIG. 6 is a cross-sectional view illustrating an example of the configuration of the scattering area 33. In the optical fiber 30 in which the scattering area 33 is configured, particles 33b are contained in the example in FIG. 5 and holes 33c are contained in the example in FIG. 6. The particles 33b and the holes 33c may be, for example, nanostructures with a diameter of 100 [nm] or smaller. The particles 33b may be, for example, fine particles or fillers, such as a microtube. In these cases, the direction in which light travels changes because of the particles 33b and the holes 33c, that is, light is scattered and accordingly the light leaks easily from the outer circumferential surface to the outside in the radial direction. The particles 33b and the holes 33c can be also referred to as scattering elements.

Figure 7:
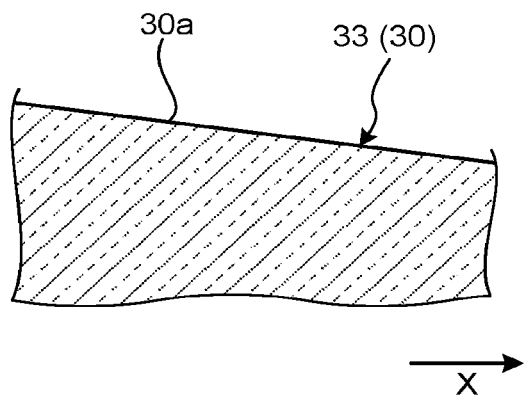
FIG. 7 is a schematic cross-sectional view of the modification of the scattering area of the radiation probe of the embodiment.

FIG. 7 is a cross-sectional view illustrating another example of the configuration of the scattering area 33. In the example in FIG. 7, the outer circumferential surface 30a of the optical fiber 30 is oblique to the X-direction that is the longitudinal direction of the optical fiber 30. The outer circumferential surface 30a is, for example, a taper surface, or the like. In a portion where the outer circumferential surface 30a changes in shape in the X-direction as described above, for example, light is incident on the portion over a critical angle and accordingly light leaks easily from the outer circumferential surface 30a to the outer side in the radial direction.

Figure 8:
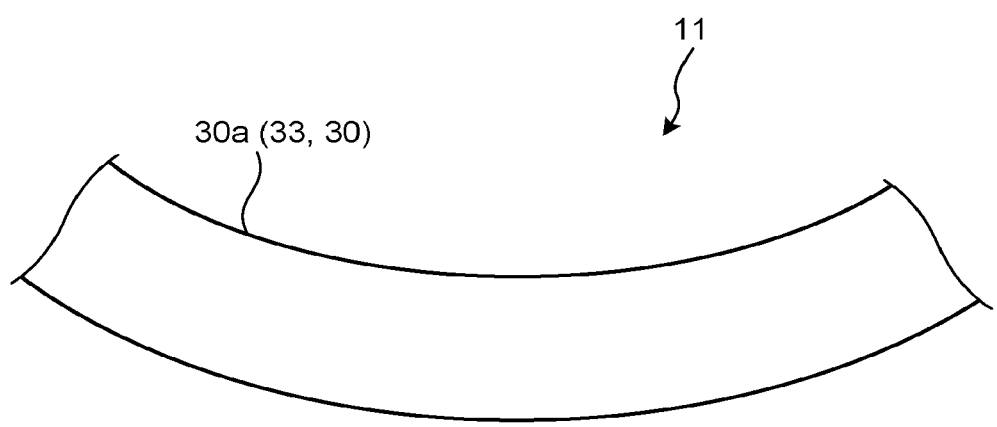
FIG. 8 is a schematic side view of the modification of the scattering area of the radiation probe of the embodiment.

FIG. 8 is a side view illustrating another example of the configuration of the scattering area 33. In the example in FIG. 8, the scattering area 33 winds. Light leaks easily from the winding portion. In other words, also with the configuration in FIG. 8, light leaks easily from the outer circumferential surface 30a to the outer side in the radial direction.

Figure 9:
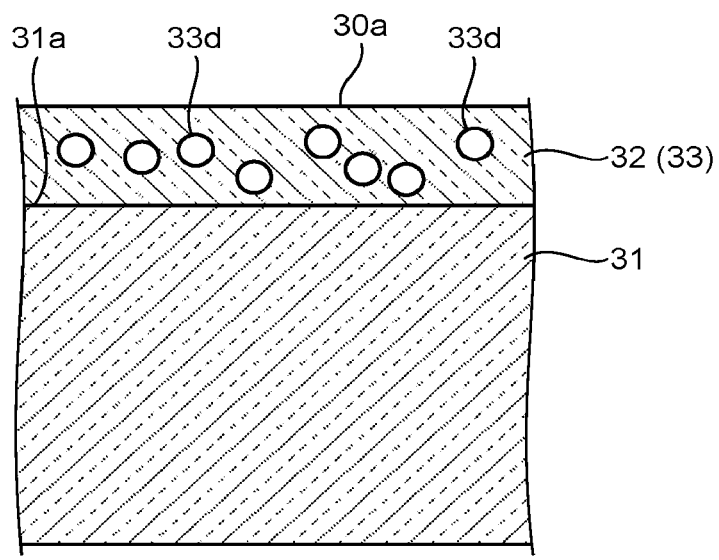
FIG. 9 is a schematic cross-sectional view of the modification of the scattering area of the radiation probe of the embodiment.

FIG. 9 is a cross-sectional view illustrating another example of the configuration of the scattering area 33. In the example in FIG. 9, the scattering area 33 has a coating layer 32 that at least partly coats an outer circumferential surface 31a of the core 31. A refractive index of the coating layer 32 is set approximately equal to or slightly higher than a refractive index of the core 31. The coating layer 32 contains scattering elements 33d, such as particles or holes. In this case, light having reached an interface between the core 31 and the coating layer 32 enters the coating layer 32, is scattered by the scattering elements 33d, and leaks to the outer side in the radial direction. According to such a configuration, for example, because of provision of the coating layer 32, an advantage that it is possible to appropriately set or change a spot where light leaks, a spot where light leaks easily, or a spot where the intensity of leaking light is high is obtained. When the coating layer 32 pressurizes the core 31 appropriately to an inner side in the radial direction, light easily leaks from the pressurized portion.

The configurations illustrated in FIGS. 5 to 9 may be combined as appropriate and practiced in the optical fiber 30.

Figure 10:
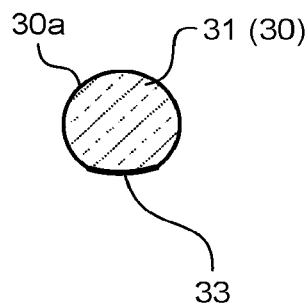
FIG. 10 is an exemplary and schematic cross-sectional view of an optical fiber of a modification of the embodiment.
Figure 10:

FIG. 10 is a cross-sectional view of the optical fiber 30 illustrating a modification of the scattering area 33. In the example in FIG. 10, an average curvature radius of the outer circumferential surface 30a in the scattering area 33 is larger than a radius of a general area of the outer circumferential surface 30a of the optical fiber 30 in which the scattering area 33 is not formed. Also in this case, the outer circumferential surface 30a is a convex curved surface in the scattering area 33.

Figure 11:
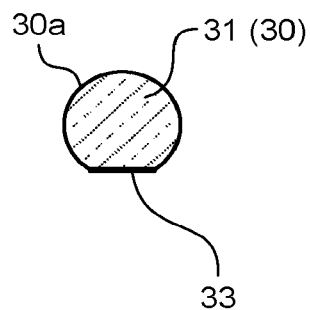
FIG. 11 is an exemplary and schematic cross-sectional view of the optical fiber of the modification of the embodiment.
Figure 11:

FIG. 11 is a cross-sectional view of the optical fiber 30 illustrating a modification of the scattering area 33. In the example in FIG. 11, the outer circumferential surface 30a in the scattering area 33 is a plane intersecting the radial direction of the optical fiber 30.

Figure 12:
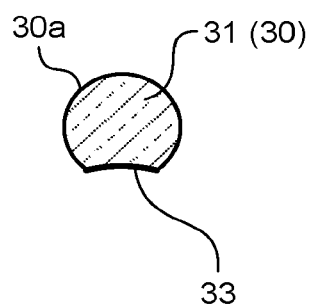
FIG. 12 is an exemplary and schematic cross-sectional view of the optical fiber of the modification of the embodiment.
Figure 12:

FIG. 12 is a cross-sectional view of the optical fiber 30 illustrating a modification of the scattering area 33. In the example in FIG. 12, the outer circumferential surface 30a in the scattering area 33 is a concave surface that is concave to the inner side in the radial direction of the optical fiber 30.

As for the various configuration examples like those in FIGS. 2 and 10 to 12, the inventors studied keenly and found that, in the optical fiber 30, it is possible to adjust a distribution ratio of a scattering light traveling in the radial direction D1 from the scattering area 33 (referred to as a first scattering light below) and a scattering light traveling in the radial direction D2 from the scattering area 33 (referred to as a second scattering light below) according to the specification of the scattering area 33. The ratio of the second scattering light to the first scattering light is referred to as a branch ratio below. The radial direction D2 is an example of a second radial direction.

Specifically, it was proved that, when the average curvature radius of the outer circumferential surface 30a in the scattering area 33 is larger than the radius of the outer circumferential surface 30a of the general area as in FIG. 10, the branch ratio can be increased compared to the case where the curvature radius of the outer circumferential surface 30a in the scattering area 33 is equal to the radius of the general area. Furthermore, it was proved that, when the outer circumferential surface 30a in the scattering area 33 is a plane or a concave surface, the branch ratio can be reduced compared to the case where the curvature radius of the outer circumferential surface 30a in the scattering area 33 is equal to the radius of the general area. Furthermore, it was proved that the magnitude of the branch ratio can be adjusted by adjusting various specifications of the scattering area 33, such as the curvature radius and a length of the scattering area 33 in the circumferential direction. Accordingly, for example, an effect that freedom in designing the radiation probe 10 increases is obtained.

In the examples in FIGS. 2 and 10 to 12, the scattering elements in the scattering area 33 can be configured as the concave portions 33a (refer to FIG. 3) that are provided on the outer circumferential surface 30a, the particles 33b (refer to FIG. 5) or the holes 33c (refer to FIG. 6) that are provided on the inner side with respect to the outer circumferential surface 30a and near the outer circumferential surface 30a, or the like.

When forming the concave portion 33a or the convex portions in the scattering area 33, it is possible to form the concave portion 33a or the convex portions by masking the outer circumferential surface 30a of the optical fiber 30 excluding the portion in which the scattering area 33 is formed and performing a process of forming an irregular surface, such as sandblasting, on the opening portion that is not masked. In this case, by performing masking at multiple stages and adjusting the time of radiation according to the direction of radiation of sandblasting, it is possible to adjust the shape and the curvature radius of the scattering area 33 appropriately.

Figure 13:
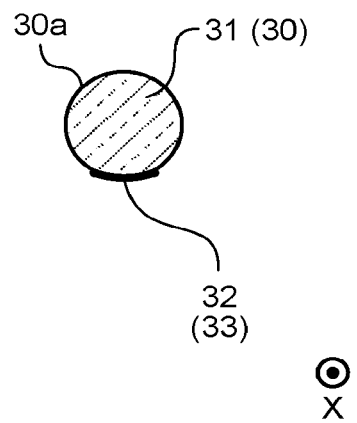
FIG. 13 is an exemplary and schematic cross-sectional view of the optical fiber of the modification of the embodiment.
Figure 14:
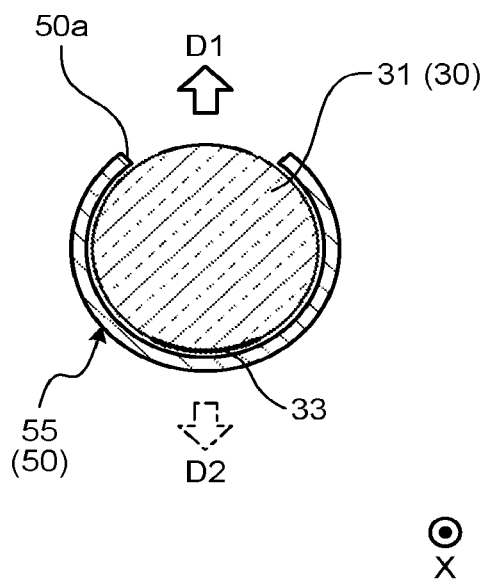
FIG. 14 is an exemplary and schematic cross-sectional view of the optical fiber and a reflective member of the modification of the embodiment.

FIG. 13 is a cross-sectional view of the optical fiber 30 illustrating a modification example of the scattering area 33. In the example in FIG. 13, the scattering area 33 is formed as the coating layer 32 illustrated in FIG. 9. Note that the coating layer 32 can be configured as part of the thin cladding layer. Also with such a configuration, it is possible to obtain the same functions and effects as those in the examples in FIGS. 2 and 10 to 12, FIG. 14 is a cross-sectional view of the optical fiber 30 illustrating a modification of the reflective member 50. In the example in FIG. 14, the reflective member 50 is configured as a sleeve 55 that partly covers the circumference of the optical fiber 30 in the leak portion 11 and that extends in the longitudinal direction. The sleeve 55 is provided with an opening 50a in a form of a slit that is open in the radial direction D1 and that extends in the longitudinal direction. As described above, the reflective member 50 can be practiced in various modes. Note that setting the reflective member 50 in a size approximately the same as that of the scattering area 33 makes it possible to make radiated light have directionality while minimizing the size of the reflective member 50. This is a configuration preferable particularly in realizing a thin radiation probe.

Figure 15:
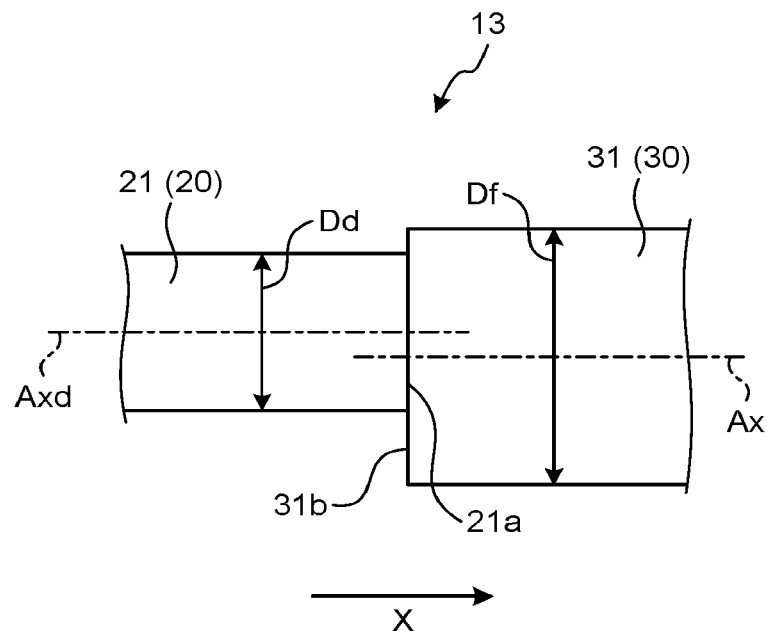
FIG. 15 is an exemplary and schematic side view of a junction between the optical fiber and a delivery optical fiber of the modification of the embodiment.

FIG. 15 is a side view of a joint 13 of the delivery optical fiber 20 and the optical fiber 30. Note that FIG. 15 illustrates a core 21 of the delivery optical fiber 20 and the core 31 of the optical fiber 30 and omits illustration of the cladding surrounding the cores 21 and 31. As in FIG. 15, in the joint 13, a center axis Axd of the core 21 of the delivery optical fiber 20 is different from the center axis Ax of the core 31 of the optical fiber 30. In other words, the delivery optical fiber 20 and the optical fiber 30 are eccentric. A diameter Dd of the core 21 of the delivery optical fiber 20 is smaller than a diameter Df of the core 31 of the optical fiber 30 and an entire facet 21a of the core 21 faces a facet 31b of the core 31. Because of consideration by the inventor, it was proved that, in such a configuration, it is possible to adjust the branch ratio by changing the amount of eccentricity between the center axes Axd and Ax. The joint 13 may be provided between the transmission portion 12 and the leak portion 11 of the radiation probe 10. In other words, the joint 13 may be provided in a connection portion between the optical fiber 30 in the transmission portion 12 and the optical fiber 30 in the leak portion 11. In this case, the optical fiber 30 in the transmission portion 12 is an example of a delivery optical fiber.

Figure 16:
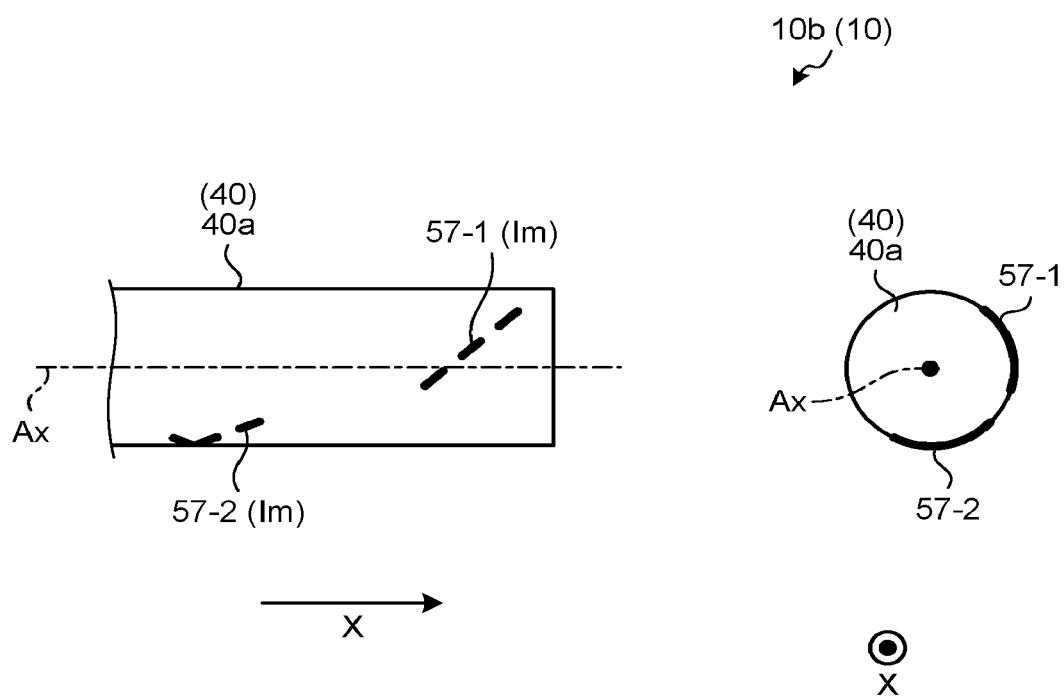
FIG. 16 is an exemplary and schematic illustration of an end of a radiation probe that is provided with a projection-subjected portion of the modification of the embodiment.
Figure 17:
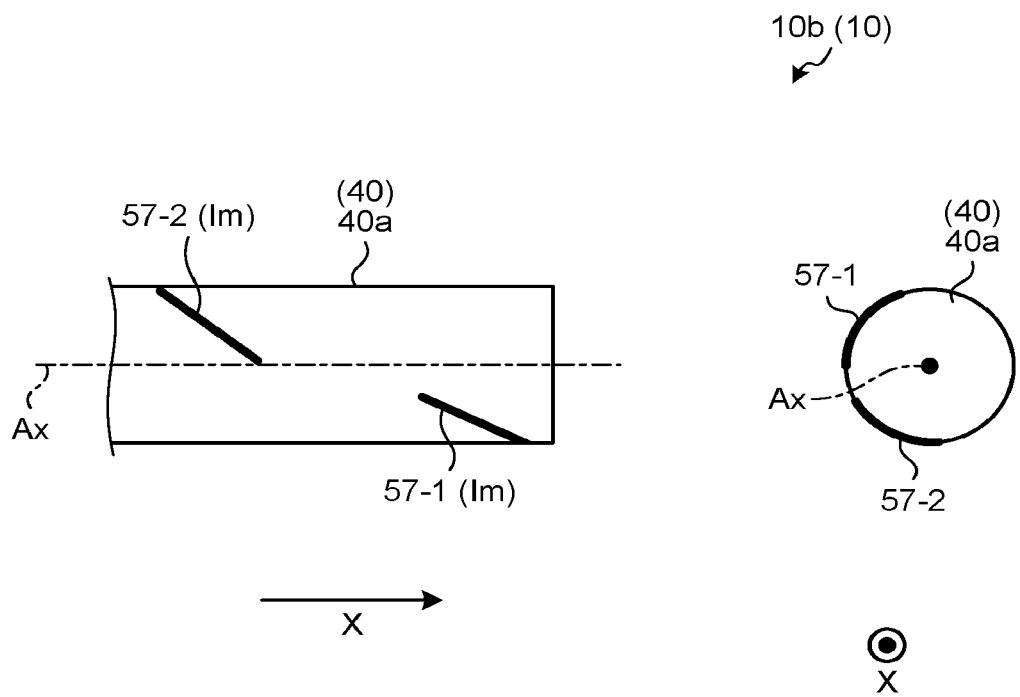
FIG. 17 is an exemplary and schematic illustration of the end of the radiation probe that is an end of the radiation probe provided with the projection-subjected portion in FIG. 16 and that has a different posture of rotation on a center axis.

FIGS. 16 and 17 are side views (left side) and front views (right side) of a modification of the end 10b of the radiation probe 10. FIG. 16 and FIG. 17 are different from each other in a posture of rotation on the center axis Ax of the radiation probe 10. In the example, markers 57-1 and 57-2 made of a metal material, or the like, are provided on an outer circumferential surface 40a of an attachment member 40 that is attached to the optical fiber 30 (not illustrated in FIG. 16) at the end 10b. The attachment member 40, for example, has transmissivity to projection light, such as X-rays, and the markers 57-1 and 57-2 have no transmissivity to projection light. In this case, a projection image Im of the markers 57-1 and 57-2 can be obtained. Arrangement of the markers 57-1 and 57-2 is set such that, when projection light is radiated from a side along the radial direction, the posture of rotation of the radiation probe 10 on the center axis Ax can be determined from the projection image Im. The markers 57-1 and 57-2 are examples of a projection-subjected portion.

When the projection-subjected portion has at least two portions that are separate from each other in the longitudinal direction of the radiation probe 10 and, when viewed in the longitudinal direction, that are separate from each other in the circumferential direction of the radiation probe 10 with a central angle different from 0 degrees or 180 degrees in between, the projection shapes of the projection-subjected portions change according to the rotation posture. In the case where the central angle is 0 degrees and 180 degrees, because there is a risk that a rotation posture with which, as for both the two portions, the widths of the projection shapes are too narrow to obtain projection shapes occurs, the case will be excluded.

In the examples in FIG. 16 and FIG. 17, the two markers 57-1 and 57-2 that are provided in the attachment member 40 separate from each other in the X-direction (longitudinal direction). The two markers 57-1 and 57-2 are separate from the center axis Ax in the radial direction and, when the markers are viewed in the longitudinal direction as illustrated on the right side in FIGS. 16 and 17, center portions are separate from each other in the circumferential direction with a central angle of approximately 90 degrees in between. Thus, in the examples in FIG. 16 and FIG. 17, the two markers 57-1 and 57-2 are an example of two portions that realize a function and an effect that make it possible to determine a rotation posture by side projection. In the example including rotation postures different from those in FIGS. 16 and 17, the different projection images Im are obtained according to the rotation postures. Thus, according to the examples in FIGS. 16 and 17, it is possible to detect a rotation posture of the radiation probe 10 relatively easily and accurately using the attachment member 40 and the markers 57-1 and 57-2.

The portions in two spots separate from each other on the markers 57-1 and 57-2 are separate from each other in the longitudinal direction and, when viewed in the longitudinal direction, separate from each other in the circumferential direction of the radiation probe 10 with a center angle different from 0 degrees or 180 degrees in between and therefore the portions can be an example of the two portions that realize the function and effect that make it possible to determine a rotation posture by side projection.

Note that the examples in FIG. 16 and FIG. 17 are examples only and the two portions and the projection-subjected portions can be practiced in various modes. For example, the two portions and the projection-subjected portions can be provided in various portions and members, such as the coating of the radiation probe 10, the reflective member 50, the cladding of the optical fiber 30, and the outer circumferential surface 31$a$ of the core 31 and the shape, arrangement, size, etc., of the two portions and the projection-subjected portions can be set variously.

As described above, according to the embodiment and the modifications described above, it is possible to realize the radiation probe 10 having directionality by which the intensity of the leaking light in the two radial directions approximately parallel to each other is higher than the intensity of the leaking light in another radial direction in the distribution of intensity of the leaking light (radiation light) in the circumferential direction, using a relatively simple configuration. Furthermore, the remarkable effect that directionality can be easily adjusted by adjusting the specification of the scattering area 33, which cannot be obtained with conventional radiation probes, is obtained. Furthermore, an advantage that it is possible to further increase directionality by radiation of the scattering light (leaking light) via the opposing surface 30$a$1 and by inputting reflected light on the reflective member 50 again is obtained.

According to the embodiment, for example, it is possible to obtain a radiation probe with an improved and novel configuration that has a small diameter and that makes it possible to obtain higher directionality and further reduce heat generation.

The embodiment of the present invention is exemplified above and the embodiment is an example and is not intended to limit the scope of the invention. The above-described embodiment can be carried out in other various modes and various types of omission, replacement, combination and change can be made without departing from the scope of the invention. Specification, such as each configuration and the shape, (the configuration, type, direction, model, size, length, width, thickness, height, number, arrangement, position, material, etc.,) can be changed as appropriate and practiced.

For example, the radiation probe may be a radiation probe that has no reflective member and that performs radiation in two radial directions.

What is claimed is:

1. A radiation probe comprising:
   an optical fiber including a leak section configured to output leaking light to an outer side in a radial direction as at least a part of a section in a longitudinal direction, wherein the optical fiber includes:
   a core,
   a cladding surrounding the core, the cladding being removed in the leak section;
   a scattering area configured to generate the leaking light by scattering light in a predetermined area in a circumferential direction of the optical fiber, the scattering area being formed on an outer circumferential surface of the core or inside the core in the leak section; and
   the optical fiber has directionality by which an intensity of the leaking light in two radial directions that are approximately parallel to each other is higher than an intensity of the leaking light in another radial direction in an intensity distribution of the leaking light in the circumferential direction in a cross-section intersecting an axial direction of the leak section.

2. The radiation probe according to claim 1, wherein an intensity of the leaking light in one of the two radial directions approximately parallel to each other and an intensity of the leaking light in the other one of the two radial directions approximately parallel to each other are different from each other.

3. The radiation probe according to claim 1, wherein the optical fiber includes, as an outer circumferential surface of the scattering area, a convex curved surface in which an average curvature radius in the scattering area is equal to or larger than a radius of a general area excluding the scattering area.

4. The radiation probe according to claim 1, wherein the optical fiber includes, as an outer circumferential surface of the scattering area, a plane intersecting the radial direction.

5. The radiation probe according to claim 1, wherein the optical fiber includes, as an outer circumferential surface of the scattering area, a concave surface that is concave to an inner side in the radial direction.

6. The radiation probe according to claim 1, comprising a delivery optical fiber configured to transmit light from a light source to the optical fiber, the delivery optical fiber being eccentric to the optical fiber, and including a core whose diameter is smaller than a diameter of a core of the optical fiber.

7. The radiation probe according to claim 1, comprising a projection-subjected portion on which a projection is made using projection light, wherein the projection-subjected portion is configured such that, when the projection light is projected in the radial direction of the radiation probe, a projection shape made by the projection light differs according to a posture of rotation on a center axis of the radiation probe.

8. The radiation probe according to claim 7, wherein the projection-subjected portion has at least two portions that are separate from each other in the longitudinal direction and, when viewed in the longitudinal direction, that are separate from each other in the circumferential direction of the radiation probe with a central angle different from 0 degrees or 180 degrees in between.

9. A radiation probe comprising:
an optical fiber including a leak section configured to output leaking light to an outer side in a radial direction as at least a part of a section in a longitudinal direction, wherein
the optical fiber includes a scattering area configured to generate the leaking light by scattering light in a predetermined area in a circumferential direction of the optical fiber in the leak section, and
the optical fiber has directionality by which an intensity of the leaking light in two radial directions that are approximately parallel to each other is higher than an intensity of the leaking light in another radial direction in an intensity distribution of the leaking light in the circumferential direction in a cross-section intersecting an axial direction of the leak section, wherein the radiation probe comprising a reflective member provided in a position differently in a first radial direction that is one of two radial directions from the leak section and configured to reflect the leaking light traveling in the first radial direction.

10. The radiation probe according to claim 9, wherein the scattering area is provided in a position differently in the first radial direction from a center axis of the optical fiber.

11. The radiation probe according to claim 10, wherein the reflective member is configured to make contact with the scattering area or faces the scattering area with a minute gap in between.

12. The radiation probe according to claim 9, wherein the scattering area is provided in a position differently in a second radial direction that is the other one of the two radial directions from a center axis of the optical fiber.

13. The radiation probe according to claim 9, wherein the optical fiber has directionality by which the intensity of the leaking light in the second radial direction that is the other one of the two radial directions is higher than the intensity of the leaking light in the first radial direction in the intensity distribution of the leaking light in the circumferential direction in the cross-section intersecting the axial direction of the leak section.

14. The radiation probe according to claim 9, wherein the leaking light traveling in the first radial direction and reflected on the reflective member enters the optical fiber and is emitted from the optical fiber to a side opposite to the reflective member.

15. The radiation probe according to claim 9, wherein the reflective member has a shape concave in the first radial direction.

16. The radiation probe according to claim 9, wherein the reflective member extends to both sides with respect to the scattering area in the circumferential direction of the optical fiber.

17. A radiation probe comprising:
an optical fiber including a leak section configured to output leaking light to an outer side in a radial direction as at least a part of a section in a longitudinal direction, wherein the optical fiber includes:
a core,
a cladding surrounding the core, the cladding being removed in the leak section,
a scattering area configured to generate the leaking light by scattering light in a predetermined area in a circumferential direction of the optical fiber, the scattering area being formed on an outer circumferential surface of the core or inside the core in the leak section; and
the optical fiber has directionality by which an intensity of the leaking light in two radial directions that are approximately parallel to each other is higher than an intensity of the leaking light in another radial direction in an intensity distribution of the leaking light in the circumferential direction in a cross-section intersecting an axial direction of the leak section.

\* \* \* \* \*